(12) United States Patent
Wilk

(10) Patent No.: US 11,257,260 B2
(45) Date of Patent: Feb. 22, 2022

(54) METHODS AND SYSTEMS FOR SCATTER CORRECTION

(71) Applicant: GE Precision Healthcare LLC, Milwaukee, WI (US)

(72) Inventor: Michael Wilk, Haifa (IL)

(73) Assignee: GE Precision Healthcare LLC, Milwaukee, WI (US)

( * ) Notice: Subject to any disclaimer, the term of this patent is extended or adjusted under 35 U.S.C. 154(b) by 20 days.

(21) Appl. No.: 16/810,638

(22) Filed: Mar. 5, 2020

(65) Prior Publication Data

US 2021/0279917 A1   Sep. 9, 2021

(51) Int. Cl.

| G06K 9/00 | (2006.01) |
|---|---|
| G06T 11/00 | (2006.01) |
| G16H 30/40 | (2018.01) |
| A61B 6/03 | (2006.01) |
| A61B 6/00 | (2006.01) |

(52) U.S. Cl.
CPC ............ *G06T 11/005* (2013.01); *A61B 6/037* (2013.01); *A61B 6/482* (2013.01); *A61B 6/5282* (2013.01); *G16H 30/40* (2018.01); *G06T 2207/10104* (2013.01); *G06T 2207/10108* (2013.01); *G06T 2207/20224* (2013.01)

(58) Field of Classification Search
CPC .................................................. G06T 11/005
See application file for complete search history.

(56) References Cited

U.S. PATENT DOCUMENTS

| 2008/0277587 | A1* | 11/2008 | Case | G06T 5/003 |
|---|---|---|---|---|
| | | | | 250/363.07 |
| 2013/0216113 | A1* | 8/2013 | O'Connor | G06T 11/60 |
| | | | | 382/128 |
| 2017/0108596 | A1* | 4/2017 | Ma | G01T 1/2985 |
| 2018/0061031 | A1* | 3/2018 | Rong | A61B 6/5235 |
| 2018/0259656 | A1* | 9/2018 | Mahani | G01T 1/1642 |

(Continued)

FOREIGN PATENT DOCUMENTS

WO    2019052816 A1    3/2019

OTHER PUBLICATIONS

Iatrou, M. et al., "3D implementation of Scatter Estimation in 3D PET," Proceedings of the 2006 IEEE Nuclear Science Symposium Conference Record, Oct. 29, 2006, San Diego, California, 4 pages.

(Continued)

*Primary Examiner* — Oneal R Mistry
(74) *Attorney, Agent, or Firm* — McCoy Russell LLP

(57) ABSTRACT

Various methods and systems are provided for scatter correction in nuclear medicine imaging systems. In one embodiment, a method for NM imaging comprises acquiring, with a plurality of detectors, imaging data separated into a high energy window and a low energy window, removing photopeak photons from the imaging data in the low energy window to obtain a corrected scatter distribution, correcting the imaging data based on the corrected scatter distribution, and outputting a scatter-corrected image reconstructed from the corrected imaging data. In this way, fast and accurate scatter correction for CZT-based gamma cameras may be performed, and image quality as well as quantitative accuracy may be increased.

21 Claims, 11 Drawing Sheets

(56) References Cited

U.S. PATENT DOCUMENTS

2019/0391282 A1* 12/2019 Hugg .................. A61B 6/0487

OTHER PUBLICATIONS

Holstensson, M. et al., "Model-based correction for scatter and tailing effects in simultaneous 99mTc and 123I imaging for a CdZnTe cardiac SPECT camera," Physics and Medicine in Biology, vol. 60. No. 8, Apr. 21, 2015, Available Online at Mar. 24, 2015, 22 pages.

* cited by examiner

METHODS AND SYSTEMS FOR SCATTER CORRECTION

FIELD

Embodiments of the subject matter disclosed herein relate to non-invasive diagnostic imaging, and in particular to scatter correction for nuclear medicine (NM) imaging systems.

BACKGROUND

Nuclear medicine (NM) imaging systems, such as positron emission tomography (PET) imaging systems and single photon emission computed tomography (SPECT) imaging systems, include multiple detectors or detector heads for detecting radiation emitted from within a subject in order to image the internal structure of the subject. For example, PET imaging systems acquire data that represent the distribution of positron-emitting nuclides within the body of a patient. When a positron interacts with an electron by annihilation, the entire mass of a positron-electron pair is converted into two 511-keV photons. The photons are emitted in opposite directions along a line of response (LOR). The annihilation photons are detected by detectors that are placed on both sides of the LOR, in a configuration such as a detector ring. Coincidence occurs when these annihilation photons arrive and are detected at the detector elements at the same time. An image is then generate based on the acquired image data that includes the annihilation photon detection information.

Compton scattering occurs when one or both annihilation photons interact with matter, change direction, and lose energy. The detection of such scattered photons causes errors and/or image artifacts. NM imaging systems are typically configured with scatter correction methods to account for Compton scattering.

BRIEF DESCRIPTION

In one embodiment, a method for NM imaging comprises acquiring, with a plurality of detectors, imaging data separated into a high energy window and a low energy window, removing photopeak photons from the imaging data in the low energy window to obtain a corrected scatter distribution, correcting the imaging data based on the corrected scatter distribution, and outputting a scatter-corrected image reconstructed from the corrected imaging data. In this way, fast and accurate scatter correction for CZT-based gamma cameras and PET may be performed, consequently increasing image quantitative accuracy.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
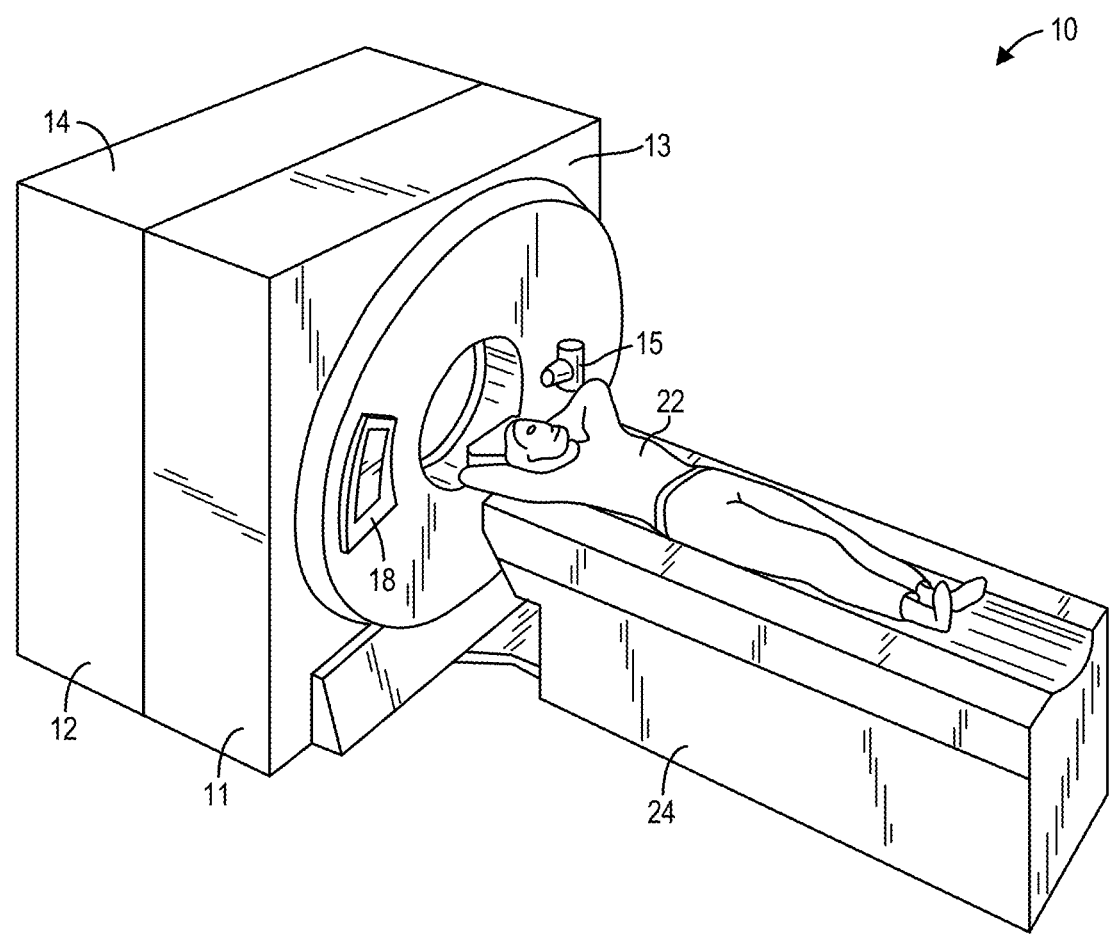
FIG. 1 shows a pictorial view of an exemplary multi-modality imaging system according to an embodiment of the invention.
Figure 2:
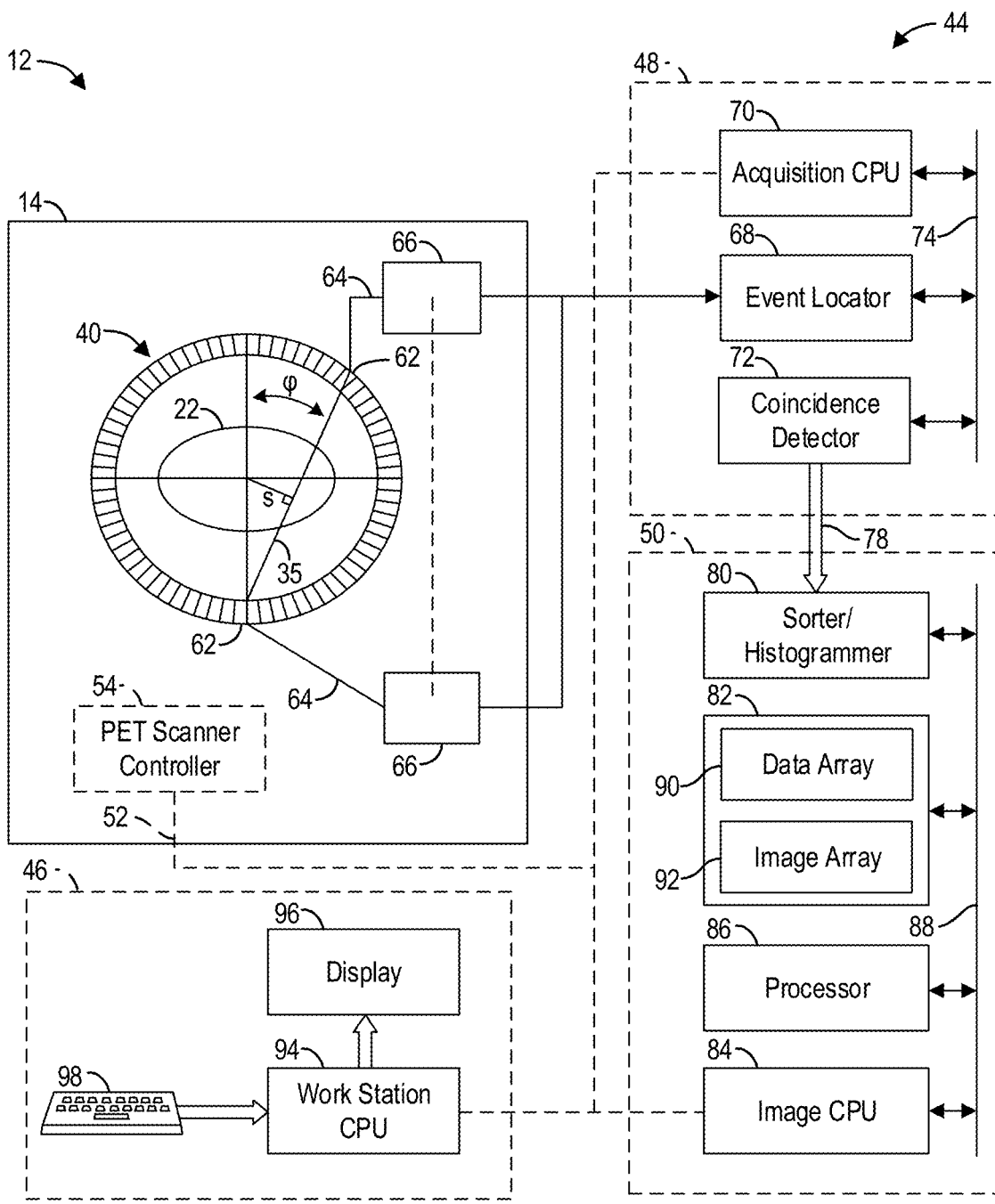
FIG. 2 shows a block schematic diagram of an exemplary imaging system with a detector, according to an embodiment of the invention.
Figure 3:
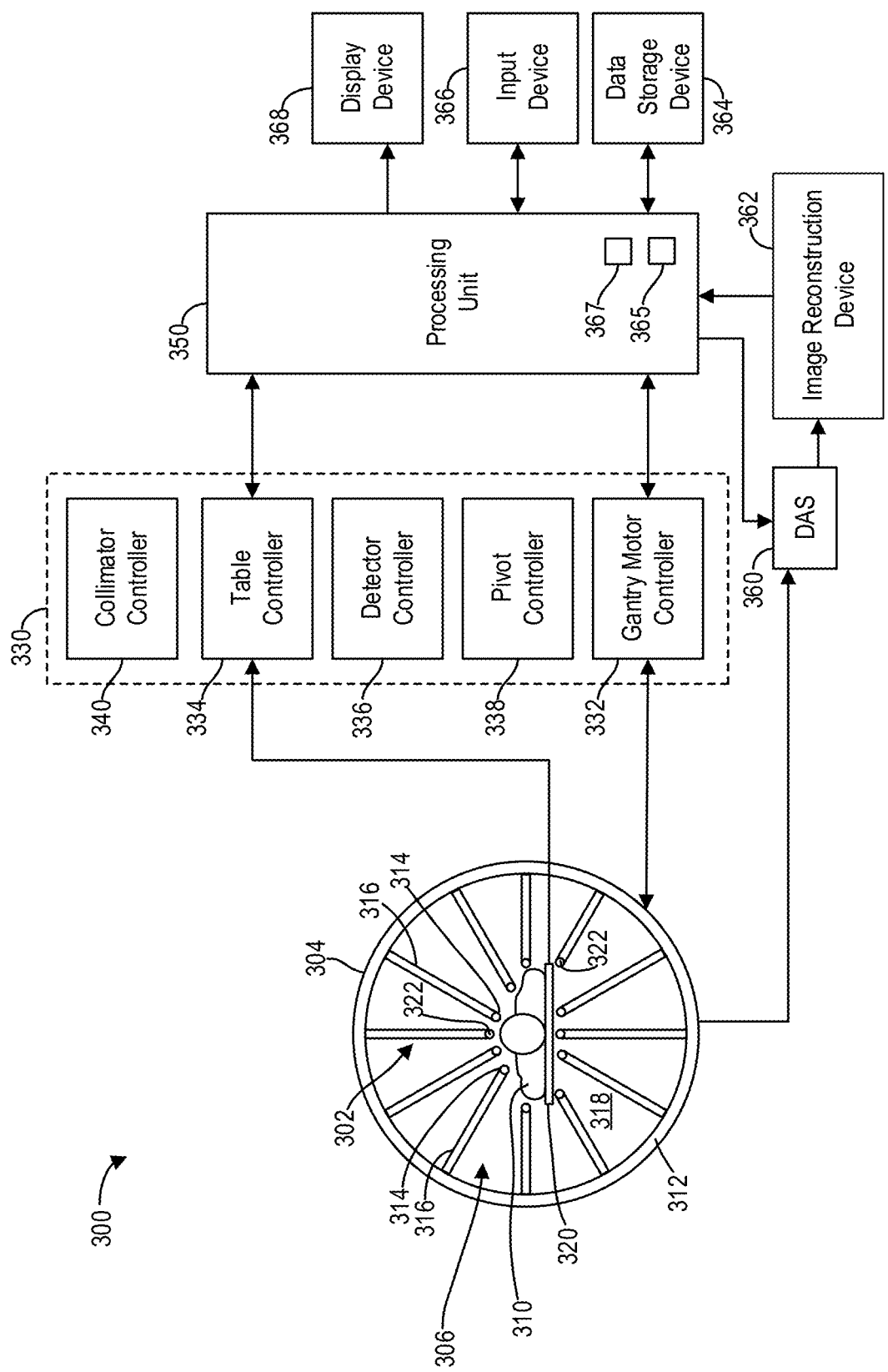
FIG. 3 is a schematic block diagram of a NM imaging system in accordance with an embodiment.
Figure 4:
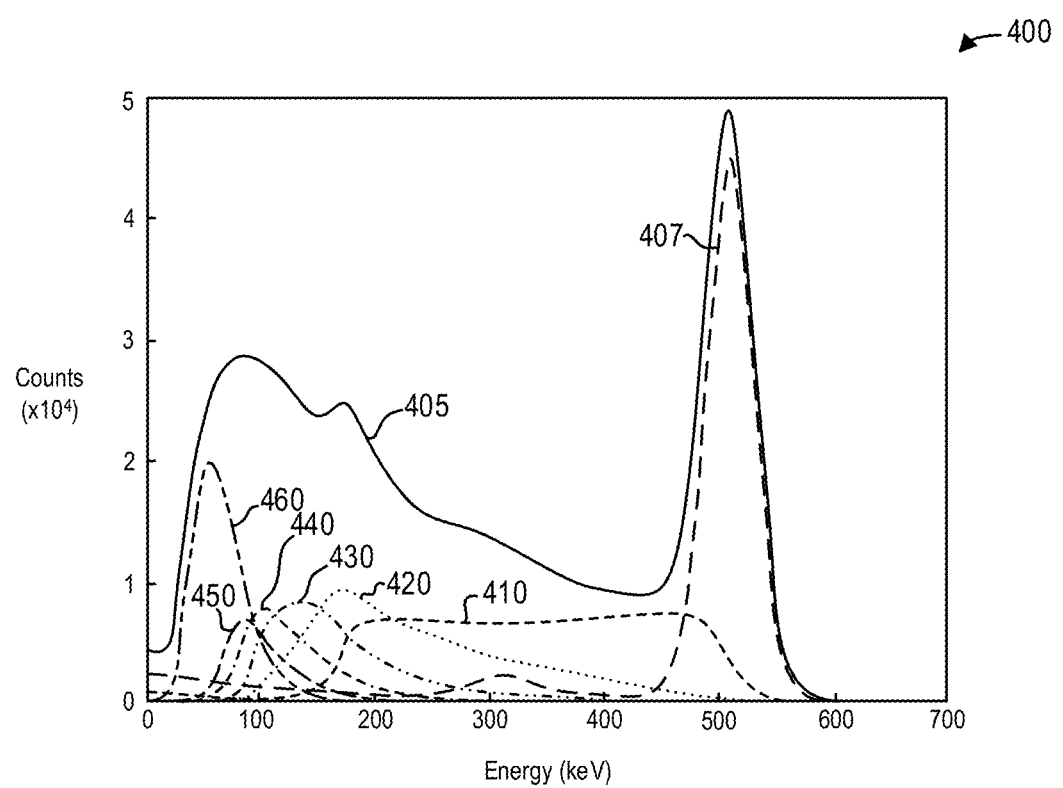
FIG. 4 shows a graph illustrating example distributions of PET scattered photons and photopeak photons acquired during a scan according to an embodiment of the invention.
Figure 5:
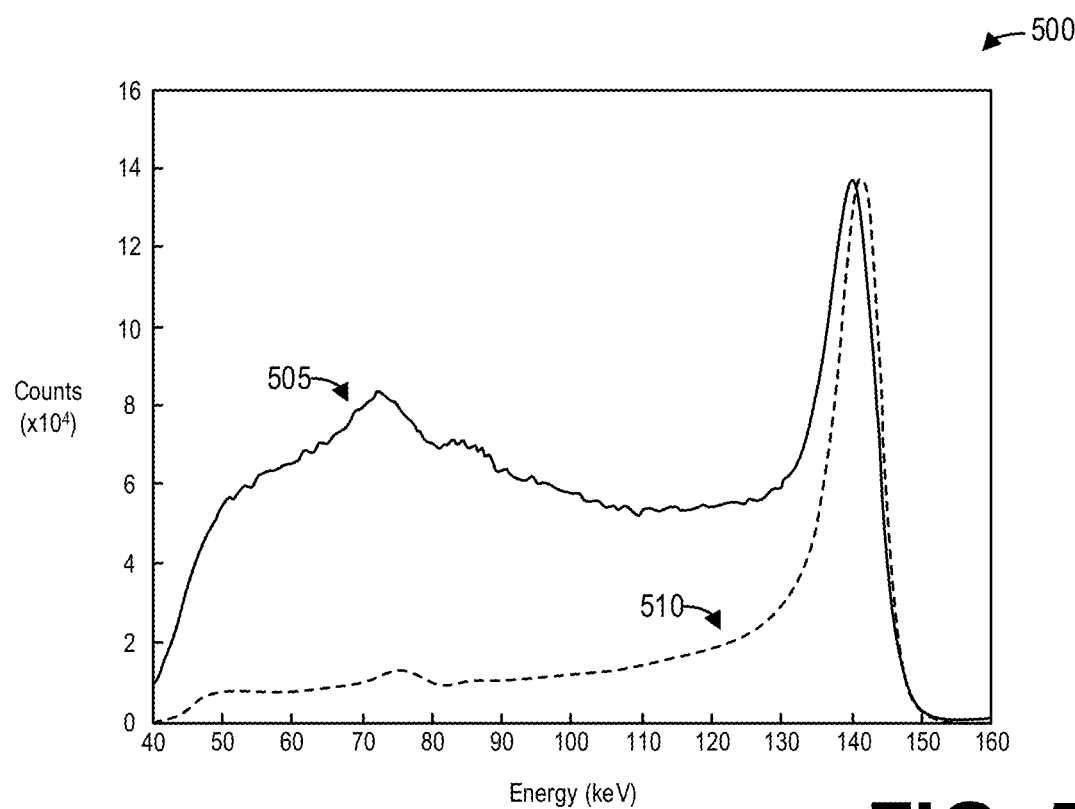
FIG. 5 shows a graph illustrating example distributions of Tc99m SPECT acquired photon counts including photopeak and only tailed photons and photopeak with tail plus scattered photon counts according to an embodiment of the invention.
Figure 8:
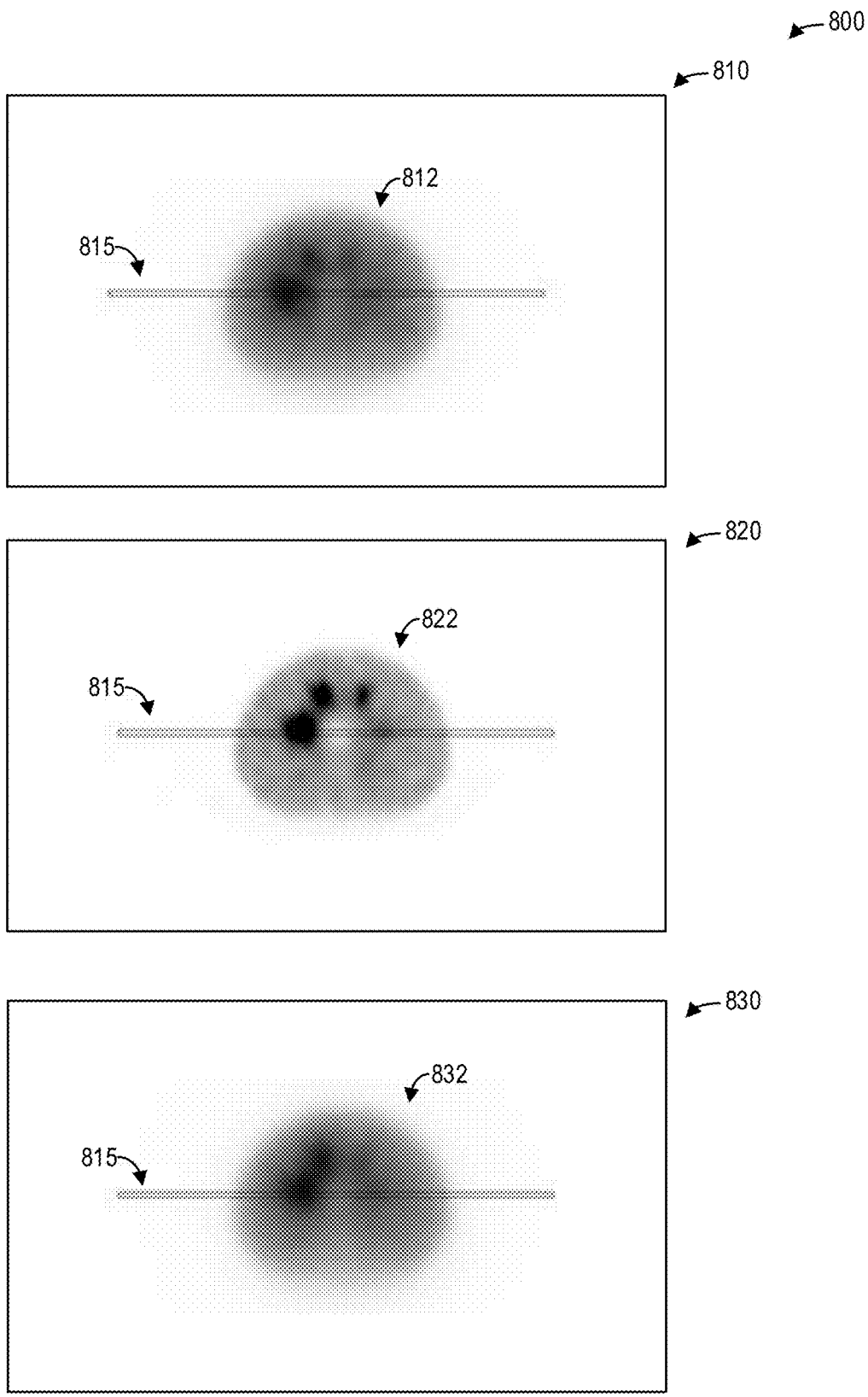
FIG. 8 shows a set of images illustrating example scatter images with and without scatter correction according to an embodiment of the invention.
Figure 9:
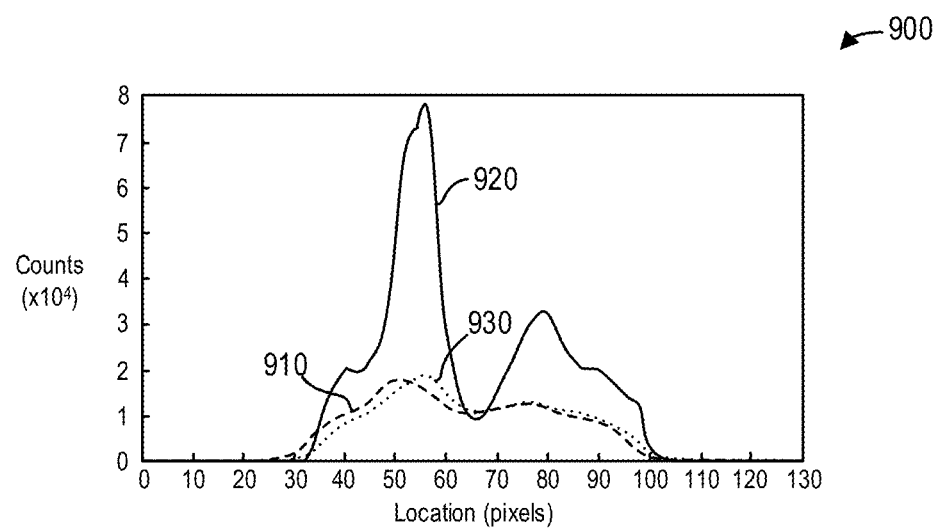
FIG. 9 shows a graph illustrating example distributions for the example scatter images of FIG. 8.
Figure 10:
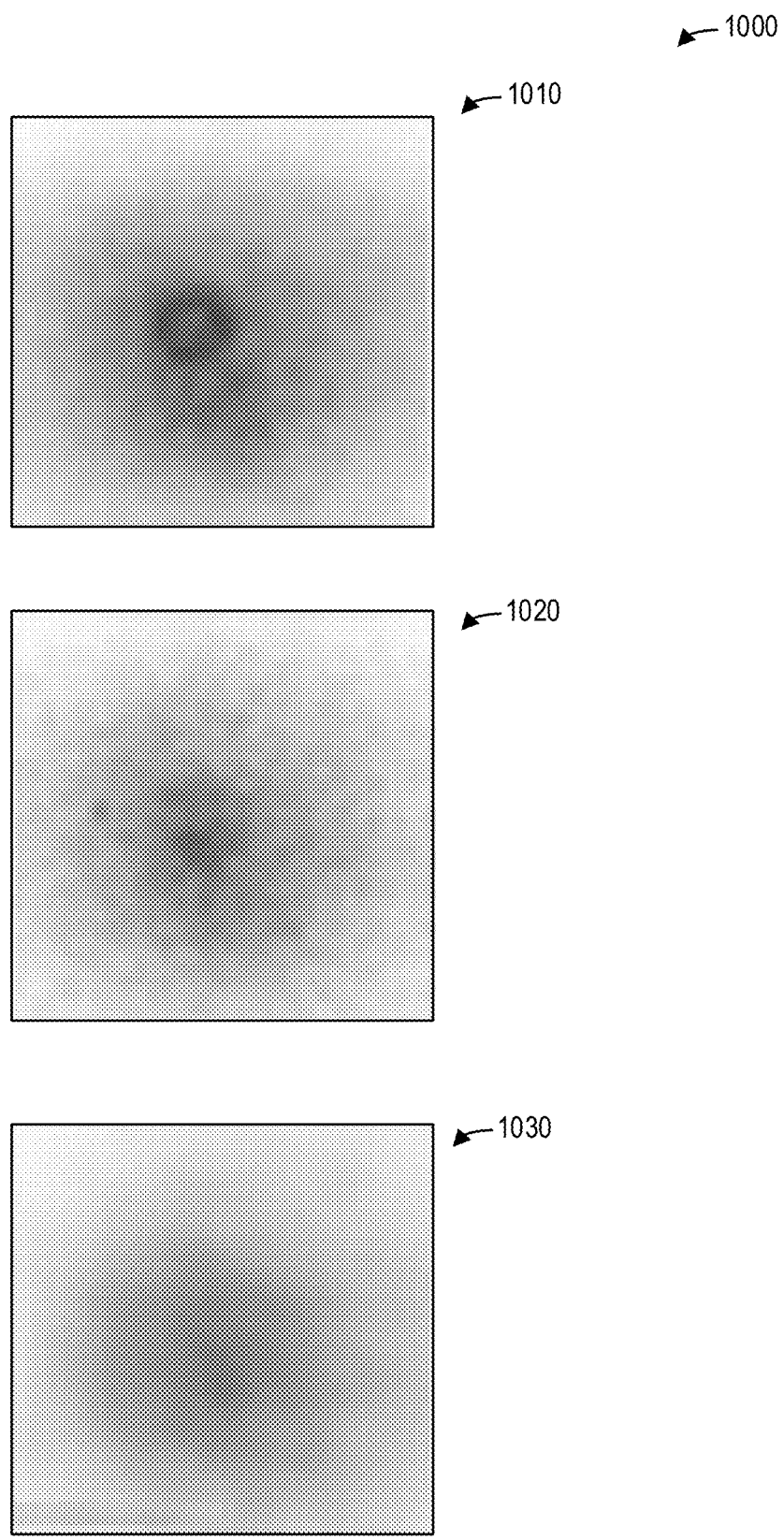
FIG. 10 shows a set of images illustrating an example scatter correction according to an embodiment.
Figure 11:
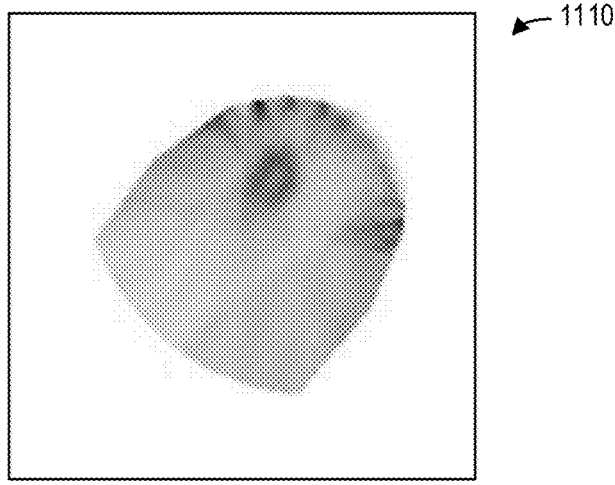
FIG. 11 shows a set of images illustrating another example scatter correction according to an embodiment.
Figure 11:
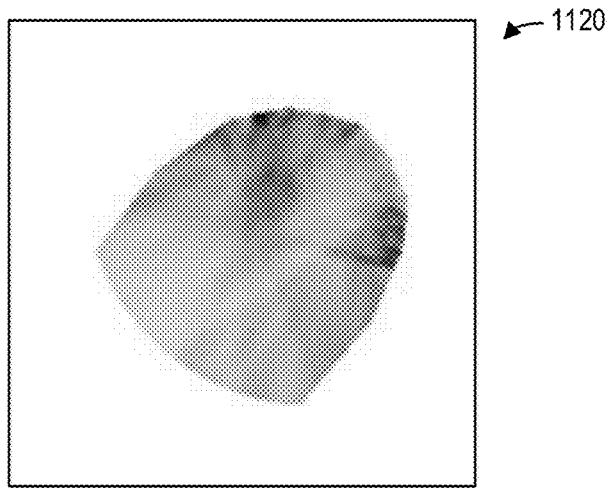
Figure 11:
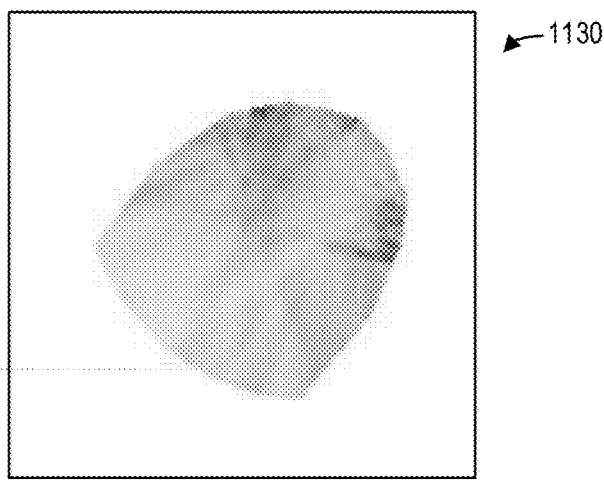

The following description relates to various embodiments of nuclear medicine (NM) imaging. In particular, methods and systems are provided for scatter correction for NM imaging systems, such as a PET or SPECT imaging system. An example of a PET imaging system that may be used to acquire images processed in accordance with the present techniques is shown in FIGS. 1 and 2. Another example of an NM imaging system that may be used to acquire images processed in accordance with the present techniques, in particular a SPECT imaging system, is shown in FIG. 3. A PET imaging system may be configured with low energy resolution detectors while a SPECT imaging system may be configured with CZT detectors which provide an improved energy resolution in comparison to more traditional NaI detectors. Further, Compton scattering occurs when one or both annihilation photons interact with matter, change direction, and lose energy. The detection of such scattered photons causes errors and/or image artifacts. The number of scattered photons may be substantial, as depicted by the example distributions of scattered photons in FIG. 4. NM imaging systems typically include scatter correction methods. Systems configured with NaI detectors, for example, may use measurements of scattered photons with an additional energy window for performing scatter correction. However, for systems configured with CZT detectors, the photopeak resolution is often asymmetric due to incomplete charge collection within the detector, resulting in many photopeak events being incorrectly sorted into lower energy bins. This "tailing" effect caused by such incorrectly binned photopeak photons, as depicted in FIG. 5, contaminates the true scatter signal in the lower energy bins, thereby negatively impacting scatter correction methods such as the multiple energy window technique mentioned hereinabove that rely on estimates of scatter from the spectra. Methods for scatter correction, such as the methods shown in FIGS. 6 and 7, include removing such tailed photopeak photons from the measurements of scattered photons to thereby obtain corrected scatter estimation. The correction methods provided herein allow for scatter measurements obtained with CZT detectors to be consistent with scatter measurements obtained with NaI detectors, as depicted in FIGS. 8 and 9. Further, the methods are applicable in projection space as well as image space, as depicted in FIGS. 10 and 11.

Various embodiments of the invention provide a multi-modality imaging system 10 as shown in FIGS. 1 and 2. Multi-modality imaging system 10 may be any type of imaging system, for example, different types of medical imaging systems, such as a Positron Emission Tomography (PET), a Single Photon Emission Computed Tomography (SPECT), a Computed Tomography (CT), an ultrasound system, Magnetic Resonance Imaging (MRI), or any other system capable of generating tomographic images. The various embodiments are not limited to multi-modality medical imaging systems, but may be used on a single modality medical imaging system such as a stand-alone PET imaging system or a stand-alone SPECT imaging system, for example. Moreover, the various embodiments are not limited to medical imaging systems for imaging human subjects, but may include veterinary or non-medical systems for imaging non-human objects.

Referring to FIG. 1, the multi-modality imaging system 10 includes a first modality unit 11 and a second modality unit 12. The two modality units enable the multi-modality imaging system 10 to scan an object or patient in a second modality using the second modality unit 12. The multi-modality imaging system 10 allows for multiple scans in different modalities to facilitate an increased diagnostic capability over single modality systems. In one embodiment, multi-modality imaging system 10 is a Computed Tomography/Positron Emission Tomography (CT/PET) imaging system 10, e.g., the first modality 11 is a CT imaging system 11 and the second modality 12 is a PET imaging system 12. The CT/PET system 10 is shown as including a gantry 13 representative of a CT imaging system and a gantry 14 that is associated with a PET imaging system. As discussed above, modalities other than CT and PET may be employed with the multi-modality imaging system 10.

The gantry 13 includes an x-ray source 15 that projects a beam of x-rays toward a detector array 18 on the opposite side of the gantry 13. Detector array 18 is formed by a plurality of detector rows (not shown) including a plurality of detector elements which together sense the projected x-rays that pass through a medical patient 22. Each detector element produces an electrical signal that represents the intensity of an impinging x-ray beam and hence allows estimation of the attenuation of the beam as it passes through the patient 22. During a scan to acquire x-ray projection data, gantry 13 and the components mounted thereon rotate about a center of rotation.

FIG. 2 is a block schematic diagram of the PET imaging system 12 illustrated in FIG. 1 in accordance with an embodiment of the present invention. The PET imaging system 12 includes a detector ring assembly 40 including a plurality of detector crystals. The PET imaging system 12 also includes a controller or processor 44, to control normalization, image reconstruction processes and perform calibration. Controller 44 is coupled to an operator workstation 46. Controller 44 includes a data acquisition processor 48 and an image reconstruction processor 50, which are interconnected via a communication link 52. PET imaging system 12 acquires scan data and transmits the data to data acquisition processor 48. The scanning operation is controlled from the operator workstation 46. The data acquired by the data acquisition processor 48 is reconstructed using the image reconstruction processor 50.

The detector ring assembly 40 includes a central opening, in which an object or patient, such as patient 22 may be positioned using, for example, a motorized table 24 (shown in FIG. 1). The motorized table 24 is aligned with the central axis of detector ring assembly 40. This motorized table 24 moves the patient 22 into the central opening of detector ring assembly 40 in response to one or more commands received from the operator workstation 46. A PET scanner controller 54, also referred to as the PET gantry controller, is provided (e.g., mounted) within PET system 12. The PET scanner controller 54 responds to the commands received from the operator workstation 46 through the communication link 52. Therefore, the scanning operation is controlled from the operator workstation 46 through PET scanner controller 54.

During operation, when a photon collides with a crystal 62 on a detector ring 40, it produces a scintillation event on the crystal. Each photomultiplier tube or photosensor produces an analog signal that is transmitted on communication line 64 when a scintillation event occurs. A set of acquisition circuits 66 is provided to receive these analog signals. Acquisition circuits 66 produce digital signals indicating the three-dimensional (3D) location and total energy of the event. The acquisition circuits 66 also produce an event detection pulse, which indicates the time or moment the scintillation event occurred. These digital signals are transmitted through a communication link, for example, a cable, to an event locator circuit 68 in the data acquisition processor 48.

The data acquisition processor 48 includes the event locator circuit 68, an acquisition CPU 70, and a coincidence detector 72. The data acquisition processor 48 periodically samples the signals produced by the acquisition circuits 66. The acquisition CPU 70 controls communications on a back-plane bus 74 and on the communication link 52. The event locator circuit 68 processes the information regarding each valid event and provides a set of digital numbers or values indicative of the detected event. For example, this information indicates when the event took place and the position of the scintillation crystal 62 that detected the event. An event data packet is communicated to the coincidence detector 72 through the back-plane bus 74. The coincidence detector 72 receives the event data packets from the event locator circuit 68 and determines if any two of the detected events are in coincidence. Coincidence is determined by a number of factors. First, the time markers in each event data packet must be within a predetermined time period, for example, 12.5 nanoseconds, of each other. Second, the line-of-response (LOR) formed by a straight line joining the two detectors that detect the coincidence event should pass through the field of view in the PET imaging system 12. Events that cannot be paired are discarded. Coincident event pairs are located and recorded as a coincidence data packet that is communicated through a physical communication link 78 to a sorter/histogrammer 80 in the image reconstruction processor 50.

The image reconstruction processor 50 includes the sorter/histogrammer 80. During operation, sorter/histogrammer 80 generates a data structure known as a histogram. A histogram includes a large number of cells, where each cell corresponds to a unique pair of detector crystals in the PET scanner. Because a PET scanner typically includes thousands of detector crystals, the histogram typically includes millions of cells. Each cell of the histogram also stores a count value representing the number of coincidence events detected by the pair of detector crystals for that cell during the scan. At the end of the scan, the data in the histogram is used to reconstruct an image of the patient. The completed histogram containing all the data from the scan is commonly referred to as a "result histogram." The term "histogrammer" generally refers to the components of the scanner, e.g., processor and memory, which carry out the function of creating the histogram.

The image reconstruction processor 50 also includes a memory module 82, an image CPU 84, an array processor 86, and a communication bus 88. During operation, the sorter/histogrammer 80 counts all events occurring along each projection ray and organizes the events into 3D data. This 3D data, or sinogram, is organized in one exemplary embodiment as a data array 90. Data array 90 is stored in the memory module 82. The communication bus 88 is linked to the communication link 52 through the image CPU 84. The image CPU 84 controls communication through communication bus 88. The array processor 86 is also connected to the communication bus 88. The array processor 86 receives data array 90 as an input and reconstructs images in the form of image array 92. Resulting image arrays 92 are then stored in memory module 82.

The images stored in the image array 92 are communicated by the image CPU 84 to the operator workstation 46. The operator workstation 46 includes a CPU 94, a display 96, and an input device 98. The CPU 94 connects to communication link 52 and receives inputs, e.g., user commands, from the input device 98. The input device 98 may be, for example, a keyboard, mouse, a touch-screen panel, and/or a voice recognition system, and so on. Through input device 98 and associated control panel switches, the operator can control the operation of the PET imaging system 12 and the positioning of the patient 22 for a scan. Similarly, the operator can control the display of the resulting image on the display 96 and can perform image-enhancement functions using programs executed by the workstation CPU 94.

The detector ring assembly 40 includes a plurality of detector units. The detector unit may include a plurality of detectors, light guides, scintillation crystals and analog application specific integrated chips (ASICs). For example, the detector unit may include twelve SiPM devices, four light guides, 144 scintillation crystals, and two analog ASICs.

As another example, FIG. 3 is a schematic illustration of a NM imaging system such as a SPECT imaging system 300 having a plurality of imaging detectors 302 mounted on a gantry 304.

The imaging detectors 302 may be configured to rotate around a fixed pivot. The movement of the imaging detectors 302 is controlled to reduce the likelihood or avoid collision among the moving imaging detectors and/or reduce the likelihood of one imaging detector obstructing the field of view of another imaging detector. For example, the SPECT imaging system 300 in some embodiments provides coordinated swinging or rotating motion of a plurality of imaging detectors 302 or detector heads.

In particular, a plurality of imaging detectors 302 are mounted to a gantry 304 and/or a patient support structure (not shown) (e.g., under a patient table 320), which may define a table support for a patient table 320. In the illustrated embodiment, the imaging detectors 302 are configured as a detector array 306 positioned around the subject 310 (e.g., a patient), as viewed in FIG. 3. The detector array 306 may be coupled directly to the gantry 304, or may be coupled via support members 312 thereto, to allow movement of the entire array 306 relative to the gantry 304 (e.g., rotational movement in the clockwise or counter-clockwise direction as viewed in FIG. 3). Additionally, each of the imaging detectors 302 includes a detector unit 314, at least some of which are mounted to a movable detector carrier 316 (e.g., a support arm or actuator that may be driven by a motor to cause movement thereof) that extends from the gantry 304. In some embodiments, the detector carriers 316 allow movement of the detector units 314 towards and away from the subject 310, such as linearly. Thus, in the illustrated embodiment the detector array 306 is around the subject 310 and may allow linear movement of the detector units 314, such as towards or away from the patient table 320 in one embodiment. However, other configurations and orientations are possible as described herein, as well as different types of movements (e.g., transverse or perpendicular movement relative to the patient table 320). It should be noted that the movable detector carrier 316 may be any type of support that allows movement of the detector units 314 relative to the support member 312 and/or gantry 304, which in various embodiments allows the detector units 314 to move linearly towards and away from the support member 312, such as radially inward and outwards for positioning adjacent the subject 310. For example, as described herein, the detector units 314 may be controlled to move independently of each other towards or away from the subject 310, as well as capable of rotational, pivoting, or tilting movement in some embodiments.

Each of the imaging detectors 302 in various embodiments is smaller than a conventional whole body or general purpose imaging detector. A conventional imaging detector may be large enough to image most or all of a width of a patient's body at one time and may have a diameter of approximately 50 cm or more. In contrast, each of the imaging detectors 302 may include one or more detector units 314 coupled to a respective detector carrier 316 and having dimensions of 4 cm to 20 cm and may be formed of Cadmium Zinc Telluride (CZT) tiles or modules. For example, each of the detector units 314 may be 8×8 cm in size and be composed of a plurality of CZT pixelated modules (not shown). For example, each module may be 4×4 cm in size and have 16×16=256 pixels. In some embodiments, each detector unit 314 includes a plurality of modules, such as an array of 1×7 modules. However, different configurations and array sizes are contemplated including, for example, detector units 314 having multiple rows of modules.

It should be understood that the imaging detectors may be different sizes and/or shapes with respect to each other, such as square, rectangular, circular, or another shape. An actual field of view (FOV) of each of the imaging detectors 302 may be directly proportional to the size and shape of the respective imaging detector.

The gantry 304 may be formed with an aperture 318 (e.g., opening or bore) therethrough as illustrated. The patient table 320 is configured with a support mechanism, such as the patient support structure, to support and carry the subject 310 in one or more of a plurality of viewing positions within the aperture 318 and relative to the imaging detectors 302. Alternatively, the gantry 304 may comprise a plurality of gantry segments (not shown), each of which may independently move a support member 312 or one or more of the imaging detectors 302.

The gantry 304 may also be configured in other shapes, such as a "C", "H", and "L", for example, and may be rotatable about the subject 310. For example, the gantry 304 may be formed as a closed ring or circle, or as an open arc or arch which allows the subject 310 to be easily accessed while imaging and facilitates loading and unloading of the subject 310, as well as reducing claustrophobia in some subjects 310. For example, in some embodiments the gantry 304 may be arc shaped and the support members 312 movable along the arc to position the detector units 314 at different locations along the gantry 304. In some embodiments, the detector units 314 may also be independently movable along the gantry 304.

Additional imaging detectors (not shown) may be positioned to form rows of detector arrays or an arc or ring around the subject 310. By positioning multiple imaging detectors 302 at multiple positions with respect to the subject 310, such as along an imaging axis (e.g., head to toe direction of the subject 310), image data specific for a larger FOV may be acquired more quickly.

Each of the imaging detectors 302 has a radiation detection face, which is directed towards the subject 310 or a region of interest within the subject 310. The radiation detection faces may be covered by or have coupled thereto a collimator 322. The actual FOV for each of the imaging detectors 302 may be increased, decreased, or relatively unchanged by the type of collimator 322. In one embodiment, the collimator 322 is a multi-bore collimator, such as a parallel-hole collimator. However, other types of collimators, such as converging or diverging collimators may optionally or alternatively be used. Other examples for the collimator 322 include pinhole, parallel-beam converging, diverging fan-beam, converging or diverging cone-beam, multi-bore converging, multi-bore converging fan-beam, multi-bore converging cone-beam, multi-bore diverging, or other types of collimators.

Optionally, multi-bore collimators may be constructed to be registered with pixels of the detector units 314, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in between two adjacent pixels may have reduced sensitivity or decreased energy resolution or other performance degradation. Having collimator septa directly above the edges of pixels reduces the chance of a photon impinging at these degraded performance locations, without decreasing the overall probability of a photon passing through the collimator.

A controller unit 330 may control the movement and positioning of the patient table 320, imaging detectors 302, gantry 304, and/or the collimators 322. A range of motion before or during an acquisition, or between different image acquisitions, is set to maintain the actual FOV of each of the imaging detectors 302 directed, for example, towards or "aimed at" a particular area or region of the subject 310 or along the entire subject 310.

The controller unit 330 may have a gantry motor controller 332, table controller 334, detector controller 336, pivot controller 338, and collimator controller 340. The controllers 330, 332, 334, 336, 338, 340 may be automatically commanded by a processing unit 350, manually controlled by an operator, or a combination thereof. The gantry motor controller 332 may move the imaging detectors 302 with respect to the subject 310, for example, individually, in segments or subsets, or simultaneously in a fixed relationship to one another. For example, in some embodiments, the gantry controller 332 may cause the imaging detectors 302 and/or one or more of the support members 312 to rotate about the subject 310, which may include motion of less than or up to 180 degrees (or more).

The table controller 334 may move the patient table 320 to position the subject 310 relative to the imaging detectors 302. The patient table 320 may be moved in up-down directions, in-out directions, and right-left directions, for example. The detector controller 336 may control movement of each of the imaging detectors 302 to move closer to and farther from a surface of the subject 310, such as by controlling translating movement of the detector carriers 316 linearly towards or away from the subject 310 (e.g., sliding or telescoping movement). Optionally, the detector controller 336 may control movement of the detector carriers 316 to allow coordinated movement of the detector array 306.

The pivot controller 338 may control pivoting, rotating, or swinging movement of the detector units 314 at ends of the detector carriers 316, and/or the detector carrier 316. For example, one or more of the detector units 314 or detector carriers 316 may be rotated or swung about at least one axis to view the subject 310 from a plurality of angular orientations. The collimator controller 340 may adjust a position of an adjustable collimator, such as a collimator with adjustable strips (or vanes) or adjustable pinhole(s).

It should be noted that motion of one or more imaging detectors 302 may be in directions other than strictly axially or radially, and optionally, motions in several motion directions may be used. Moreover, the motions of the imaging detectors 302 are coordinated in various embodiments as described herein. Therefore, the term "motion controller" may be used to indicate a collective name for all motion controllers. It should be noted that the various controllers may be combined, for example, the detector controller 336 and pivot controller 338 may be combined to provide the different movements described herein.

Prior to acquiring an image of the subject 310 or a portion of the subject 310, the imaging detectors 302, gantry 304, patient table 320, and/or collimators 322 may be adjusted as discussed in more detail herein, such as to first or initial imaging positions, as well as subsequent imaging positions. The imaging detectors 302 may each be positioned to image a portion of the subject 310. Alternatively, one or more of the imaging detectors 302 may not be used to acquire data, such as the imaging detectors 302 at ends of the detector array 306, which as illustrated in FIG. 3 are in a protracted position towards the subject 310. Positioning may be accomplished manually by the operator and/or automatically, which may include using other images acquired before the current acquisition, such as by another imaging modality such as CT, MM, X-ray, PET, or ultrasound.

After the imaging detectors 302, gantry 304, patient table 320, and/or collimators 322 are positioned, one or more images are acquired by one or more of the imaging detectors 302 being used, which may include pivoting or swinging motion of one or more of the detector units 314, which may pivot, rotate, or swing to different degrees or between different ranges of angles. The image data acquired by each imaging detector 302 may be combined and reconstructed into a composite image, which may comprise two-dimensional (2D) images, a three-dimensional (3D) volume, or a 3D volume over time (4D).

In one embodiment, the imaging detectors 302, gantry 304, patient table 320, and/or collimators 322 remain stationary after being initially positioned. In another embodiment, an effective field of view for one or more of the imaging detectors may be increased by movement such as pivoting, rotating, or swinging one or more of the imaging detectors 302, rotating the detector array 306 with the gantry 304, adjusting one or more of the collimators 322, or moving the patient table 320.

In various embodiments, a data acquisition system (DAS) 360 receives electrical signal data produced by the imaging detectors 302 and converts this data into digital signals for subsequent processing. An image reconstruction device 362 and a data storage device 364 may be provided in addition to the processing unit 350. It should be noted that one or more functions related to one or more of data acquisition, motion control, data processing, and image reconstruction may be accomplished through hardware, software, and/or by shared processing resources, which may be located within or near the imaging system 300, or may be located remotely. Additionally, a user input device 366 may be provided to receive user inputs (e.g., control commands), as well as a display 368 for displaying images.

Additionally, a detector position controller 365 is also provided, which may be implemented in hardware, software, or a combination thereof. For example, as shown in FIG. 3, the detector position controller 365 may form part of or operate in connection with the processing unit 350. In some embodiments, the detector position controller 365 may be a module that operates to control the movement of the imaging detectors 302, including the detector units 314, such that coordinated or synchronized movement is provided as described herein. It should be noted that movement of a plurality of the imaging detectors 302 and/or detector units 314 may be performed at the same time (e.g., simultaneously or concurrently) or at different times (e.g., sequentially or step-wise, such as back and forth between two detector units 314). It also should be understood that when referring to a detector head, such a detector head may include one or multiple detector modules.

As mentioned hereinabove, Compton scattering occurs when one or both annihilation photons interact with matter (e.g., the patient 22 or the subject 310), change direction, and lose energy. The detection of such scattered photons causes errors and/or image artifacts. An NM imaging system such as the PET imaging system 12 or the SPECT imaging system 300 may therefore be configured to perform scatter correction to reduce errors or image artifacts caused by scattered photons. Scatter correction may be based on measurements of scattered photons or scatter simulations based on emission and attenuation information. For example, one approach to scatter correction is based on the use of multiple energy windows, wherein the information from other windows is used to estimate the scatter within the photopeak window, and the estimated scatter is subtracted from the photopeak window. This approach works relatively well for NaI detectors with a modest 10% energy resolution, for example. However, for CZT gamma cameras which offer significantly improved energy resolution in comparison to traditional NaI detectors, the photopeak resolution is often asymmetric due to incomplete charge collection within the detector, resulting in many photopeak events being incorrectly sorted into lower energy bins. This "tailing" effect caused by such incorrectly binned photopeak photons contaminates the true scatter signal in the lower energy bins, thereby negatively impacting scatter correction methods such as the multiple energy window technique mentioned hereinabove that rely on estimates of scatter from the spectra.

As described further herein, systems and methods are provided for scatter correction based on a decomposition of photopeak and scattered photons acquired in two or more energy windows. As an illustrative example of how photopeak and scattered photons may be distributed over a range of energies and thus decomposed as described further herein, FIG. 4 shows a graph 400 illustrating example distributions of scattered photons and photopeak photons acquired or measured with PET detectors during a scan according to an embodiment of the invention. Graph 400 includes a plot of the total distribution 405 of photon counts, including both scattered photons and photopeak photons. Graph 400 further includes a plot of the photopeak distribution 407 of the photopeak photons, a plot of the first scatter distribution 410 for first-order scattered photons, a plot of the second scatter distribution 420 for second-order scattered photons, a plot of the third scatter distribution 430 for third-order scattered photons, a plot of the fourth scatter distribution 440 for fourth-order scattered photons, a plot of the fifth scatter distribution 450 for fifth-order scattered photons, and a plot of the sixth scatter distribution 460 for sixth-order scattered photons.

The photopeak distribution 407 clearly illustrates the so-called photopeak comprising the primary gamma photon energy, which comprises 511 keV in the example but may comprise a different energy in other examples, such as for SPECT, depending on the radionuclide(s). Notably, the total distribution 405 at the photopeak energy is higher than the photopeak distribution 407, due to contributions from scattered photons.

At lower energies, the total distribution 405 is substantial but is mostly composed of scattered photons as indicated by the distributions 410, 420, 430, 440, 450, and 460. However, the photopeak distribution 407 is non-zero in this scatter region due to the tailing effect mentioned hereinabove, and so the total distribution 405 at lower energies includes contributions from photopeak photons in the photopeak distribution 407.

As described further herein, the photopeak photons may be removed from the lower energy bins, for example at a scatter window or low energy window positioned near 120 keV in the case of SPECT Tc99m imaging, in order to obtain corrected scatter data. This corrected scatter data in turn may be used to correct the photopeak window or high energy window, or the photopeak distribution 407 near the photopeak energy, such that a scatter-free image may be obtained.

FIG. 5 shows a graph 500 illustrating example distributions of scattered and photopeak photons acquired or measured with CZT detectors in a SPECT imaging system, such as the SPECT imaging system 300, according to an embodiment. In particular, graph 500 includes a plot of the total distribution 505 of the photon counts, including both scattered and photopeak photons, as well as a plot of the photopeak distribution 510 of the photopeak photons. Both distributions 505 and 510 clearly illustrate the photopeak comprising the primary gamma photon energy. The total distribution 505 further clearly depicts the tailing effect of scattered photons on the distribution when compared to the pure photopeak distribution 510.

As an illustrative example of how the photopeak distribution and the scatter distributions may be decomposed, the total amount of photons HW in the high energy window may be expressed as:

$$HW = P + \beta^* S,$$

while the total number of photons LW in the low energy window may be expressed as:

$$LW = \alpha^* P + S,$$

where P is the number of photopeak photons in the high energy window, S is the number of scattered photons in the low energy window, β*S is the number of scattered photons in the high energy window, and α*P is the number of photopeak photons in the low energy window. The scaling factors α and β are both less than one. The scaling factor α may be measured during calibration of the detector without scattered media, while the scaling factor β may be measured during calibration on phantom data based on the width and position of the high and low energy windows.

The distribution of scattered photons SD may thus be obtained by multiplying the total number of photons HW in the high energy window by the scaling factor α and subtracting the result from the total number of photons LW in the low energy window, such that:

$$SD = LW - \alpha*HW = (1-\alpha*\beta)*S.$$

Since both scaling factors α and β are less than one, the product of α and β is less than one, and the factor $(1-\alpha*\beta)$ is therefore greater than 0 and less than one. An estimate of the amount of photons S in the scatter window may thus be obtained by dividing the resulted amount of scattered photons in SD by the factor $(1-\alpha*\beta)$.

Figure 6:
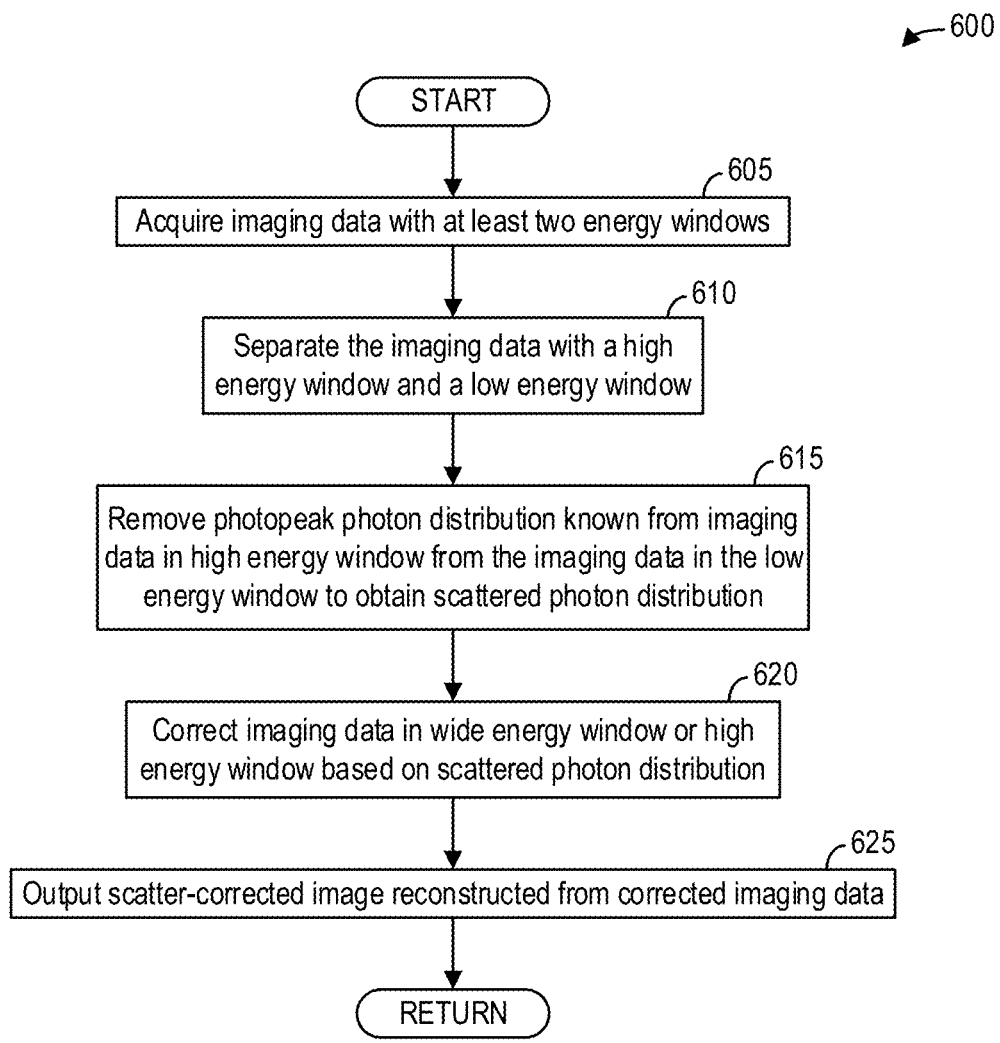
FIG. 6 shows a high-level flow chart illustrating an example method for scatter correction according to an embodiment of the invention.

Various methods are provided herein for improved scatter correction by considering tailed photopeak photons. As an example, FIG. 6 shows a high-level flow chart illustrating an example method 600 for scatter correction according to an embodiment of the invention. In particular, method 600 relates to removing photopeak photons from a scatter window to improve scatter correction of a photopeak window in an acquired imaging dataset. Method 600 is described with regard to the systems and components of FIGS. 1-3, though it should be appreciated that the method 600 may be implemented with other systems and components without departing from the scope of the present disclosure. Method 600 may be implemented as executable instructions in memory, such as non-transitory memory of the memory module 82, and executed by one or more processors such as the acquisition CPU 70, the image CPU 84, and the array processor 86, as an illustrative and non-limiting example. As another illustrative and non-limiting example, method 600 may be implemented as executable instructions in memory, such as non-transitory memory of the data storage device 364, and executed by one or more processors such as the processing unit 350 and/or the image reconstruction device 362.

Method 600 begins at 605. At 605, method 600 acquires imaging data with at least two energy windows. For example, method 600 acquires the imaging data in accordance with a nuclear medicine imaging protocol such as a single-photon emission computed tomography (SPECT) imaging protocol or a positron emission tomography (PET) imaging protocol. In some examples, method 600 acquires the imaging data with a wide energy window, wherein the wide energy window is sufficiently wide enough (e.g., includes a large enough range of energy bins) to cover at least two energy windows that do not overlap. One energy window of the at least two energy windows comprises a photopeak window including a threshold range of energies around the photopeak energy. A second window of the at least two energy windows comprises a scatter window including a threshold range of energies, wherein the threshold range of energies is displaced away from the photopeak energy such that the threshold range of energies for the scatter window does not overlap with the threshold range of energies for the photopeak window. As the photopeak energy is typically near the higher end of the range of energy bins measured during a scan, the photopeak window may also be referred to herein as a high energy window. Similarly, scatter photons typically have a lower energy in comparison to photopeak photons due to the scattering, and so the scatter window is also referred to herein as a low energy window. Continuing at 610, method 600 separates the imaging data with a high energy window and a low energy window. The high energy window may comprise the photopeak window, while the low energy window may comprise the scatter window as discussed hereinabove.

At 615, method 600 removes the photopeak photon distribution known from the imaging data in the high energy window from the imaging data in the low energy window to obtain a scattered photon distribution. That is, method 600 estimates the distribution of photopeak photons in the low energy window based on the imaging data in the high energy window that primarily contains photopeak photons, and removes the photopeak photons from the imaging data in the low energy window. Such an approach is possible because photopeak photons have the same spatial distribution in both the high and low energy windows. In this way, the corrected imaging data in the low energy window corresponds to scatter photons only, and thus may be used for a more accurate scatter correction of the imaging data in the high energy window. In some examples, method 600 uses an image-based subtraction method to remove the photopeak photon distribution from the imaging data of the low energy window. An example image-based subtraction method is described further herein with regard to FIG. 7. In other examples, method 600 may remove the photopeak photon distribution from the low energy window by applying a correction of the two datasets during iterative reconstruction. In yet other examples, method 600 may remove the photopeak photon distribution from the low energy window by applying a correction to the low energy window during iterative post-reconstruction processing. For example, to apply the correction during iterative reconstruction, method 600 may reconstruct the pure scatter image with an iterative algorithm such as Expectation-Maximization (EM). During reconstruction, method 600 may add weighted projections of the high energy peak to calculated forward projections of the low energy peak:

$$REC^n = REC^{n-1} * \frac{1}{NORM} * Backproject\left[\frac{LPP}{Forward(REC^{n-1}) + w*HPP}\right],$$

where REC is the reconstructed pure scatter image, n is the iteration number, NORM is a normalization factor, LPP is low peak projections, Forward($Rec^{n-1}$) is the forwarded projections of the (n−1) iteration, and w is the weight of the high peak projection (HPP).

As another example, to apply the correction during iterative post-reconstruction processing, method 600 may reconstruct low energy images (LEI) and high energy images (HEI) separately, and, starting with LEI, iteratively calculate a "pure" scatter image S:

$$S^n = S^{n-1} * \frac{LEI}{[(1-\alpha)*S^{n-1} + \alpha*HEI]}.$$

At 620, method 600 corrects the imaging data in the wide energy window or the high energy window based on the scattered photon distribution. In some examples, method 600 may correct the imaging data by using an image-based or a projection-based subtraction technique, during the process of iterative reconstruction, or in iterative post-processing. For example, the corrected imaging data of the lower energy window (i.e., the corrected scatter projections) may be subtracted from the imaging data or the projection data of the high energy window. As another example, the corrected scatter projections may be used to estimate the scatter in the high energy window, for example by scaling or weighting the corrected scatter projections, and then this estimated scatter in the high energy window may be used during iterative reconstruction by adding the estimated scatter to an estimated scatter-free projection to match the acquired projections or imaging data of the high energy window.

At 625, method 600 outputs a scatter-corrected image reconstructed from the corrected imaging data. For example, method 600 may obtain the scatter-corrected image at 620 when correcting the imaging data in the high energy window based on the scattered photon distribution, and so method 600 may output the scatter-corrected image to a display device, such as display 96, or to a non-transitory memory for storage and later retrieval. As another example, if corrected projection data for the high energy window is obtained at 620, method 600 may reconstruct the corrected projection data based on an image reconstruction technique such as iterative reconstruction, analytic reconstruction (e.g., filtered back projection), or a deep learning image reconstruction model. Method 600 then returns.

Figure 7:
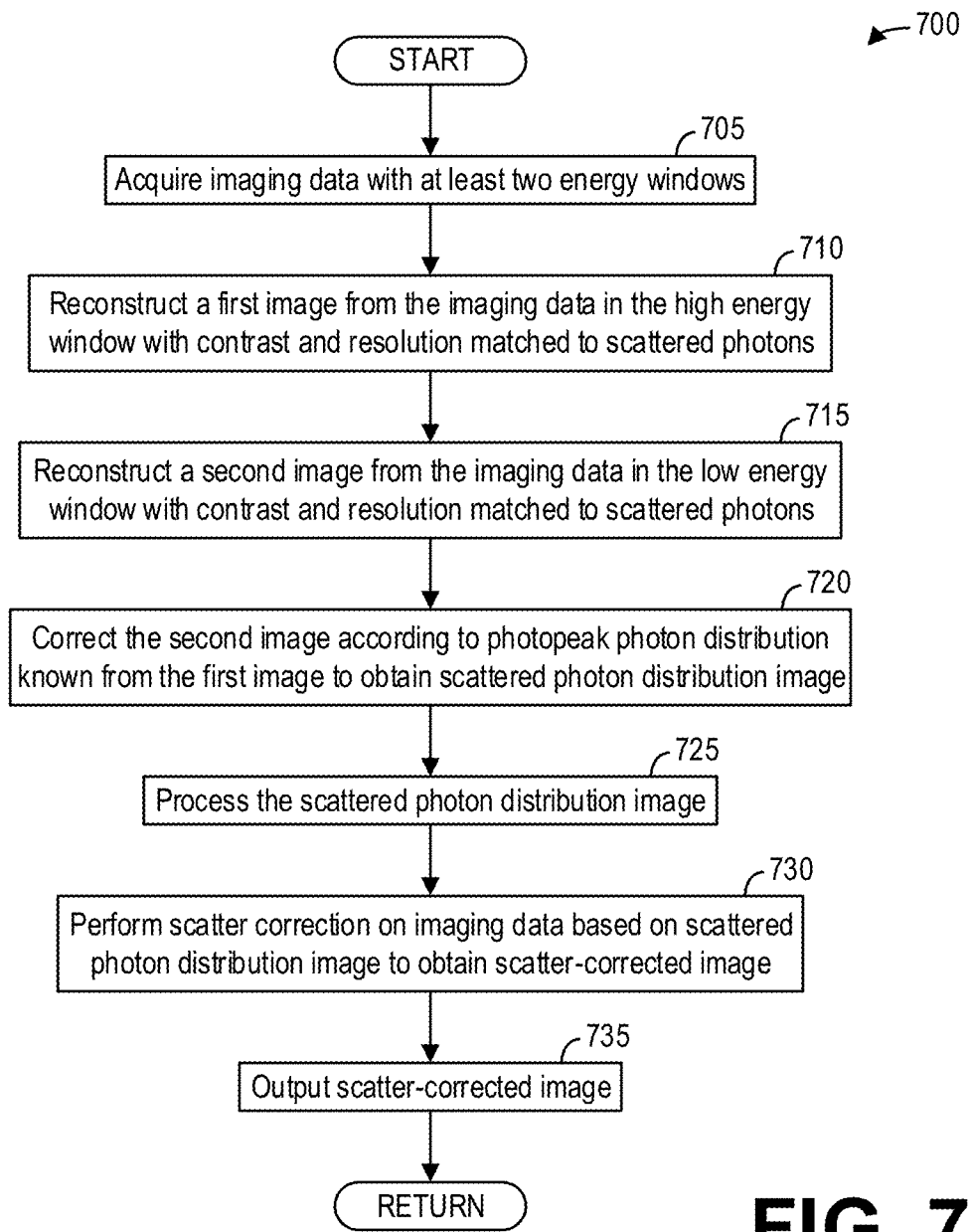
FIG. 7 shows a high-level flow chart illustrating an example method for scatter correction according to an embodiment of the invention.

FIG. 7 shows a high-level flow chart illustrating an example method 700 for scatter correction according to an embodiment of the invention. In particular, method 700 relates to an image-based technique for correcting a scatter estimate in order to improve scatter correction. Method 700 is described with regard to the systems and components of FIGS. 1-3, though it should be appreciated that the method 700 may be implemented with other systems and components without departing from the scope of the present disclosure. Method 700 may be implemented as executable instructions in memory, such as non-transitory memory of the memory module 82, and executed by one or more processors such as the acquisition CPU 70, the image CPU 84, and the array processor 86, as an illustrative and non-limiting example. As another illustrative and non-limiting example, method 600 may be implemented as executable instructions in memory, such as non-transitory memory of the data storage device 364, and executed by one or more processors such as the processing unit 350 and/or the image reconstruction device 362.

Method 700 begins at 705. At 705, method 700 acquires imaging data with at least two energy windows. For example, method 700 acquires the imaging data in accordance with a nuclear medicine imaging protocol such as a single-photon emission computed tomography (SPECT) imaging protocol or a positron emission tomography (PET) imaging protocol. As discussed hereinabove, one energy window of the at least two energy windows comprises a photopeak window including a threshold range of energies around the photopeak energy. A second window of the at least two energy windows comprises a scatter window including a threshold range of energies, wherein the threshold range of energies is displaced away from the photopeak energy such that the threshold range of energies for the scatter window does not overlap with the threshold range of energies for the photopeak window. As the photopeak energy is typically near the higher end of the range of energy bins measured during a scan, the photopeak window may also be referred to herein as a high energy window. Similarly, scatter photons typically have a lower energy in comparison to photopeak photons due to the scattering, and so the scatter window is also referred to herein as a low energy window.

At 710, method 700 reconstructs a first image from the imaging data in the high energy window with a contrast and resolution matched to scattered photons. For example, method 700 may reconstruct the first image by perform iterative reconstruction with the imaging data of the high energy window for a limited number of iterations, such as two or three iterations, such that the first image is reconstructed at a low resolution with a primarily low frequency signal. As typical scattered photon distributions do not have high frequencies and are primarily low frequency, the contrast and resolution is thus matched to the scattered photon distribution.

Similarly, at 715, method 700 reconstructs a second image from the imaging data in the low energy window with a contrast and resolution matched to scattered photons. For example, method 700 may perform iterative reconstruction with the imaging data of the low energy window for a limited number of iterations, such as two or three iterations, such that the second image is reconstructed with the low resolution matched to a typical scattered photon distribution.

At 720, method 700 corrects the second image according to a photopeak photon distribution known from the first image to obtain a scattered photon distribution image. For example, method 700 may subtract the first image from the second image to obtain the scattered photon distribution image. In particular, method 700 may perform a weighted subtraction, wherein the first image is weighted by the scaling factor α described hereinabove to obtain a scattered photon distribution image SD from the first image HW and the second image LW:

$$SD = LW - \alpha * HW,$$

where the scaling factor α is obtained from detector calibration without scatter media, as discussed hereinabove.

Continuing at 725, method 700 processes the scattered photon distribution image (e.g., the image SD obtained via the subtraction method at 720). For example, method 700 may scale the image by multiplying the image by the inverse of the factor $(1-\alpha*\beta)$ described hereinabove.

At 730, method 700 performs scatter correction on the imaging data based on the scattered photon distribution image to obtain a scatter-corrected image. In some examples, method 700 may correct the imaging data by using an image-based or a projection-based subtraction technique, during the process of iterative reconstruction, or in iterative post-processing. For example, the corrected imaging data of the lower energy window (i.e., the corrected scatter projections) may be subtracted from the imaging data or the projection data of the high energy window. As another example, the corrected scatter projections may be obtained by transforming the processed scattered photon distribution image to projection space to obtain processed scattered photon distribution projections, and these corrected scatter projections may be used to estimate the scatter in the high energy window, for example by scaling or weighting the corrected scatter projections, and then this estimated scatter in the high energy window may be used during iterative reconstruction by adding the estimated scatter to an estimated scatter-free projection to match the acquired projections or imaging data of the high energy window.

At 735, method 700 outputs the scatter-corrected image, for example to the display 96 or to storage for later retrieval. Method 700 then returns.

FIG. 8 shows a set of images 800 illustrating example scatter images with and without scatter correction according to an embodiment of the invention. Each of the scatter images 800 are acquired of a same subject (e.g., a same phantom) and are reconstructed with a same technique from a same energy window, and depict a same region of interest (ROI) 815 overlaid on each image. in particular, the set of images 800 includes a scatter image 810 acquired with a sodium iodine (NaI) gamma camera, such that the scatter image 810 does not include tailed photons. The correction methods described hereinabove therefore may not be applicable to the scatter image 810, as the scatter image 810 does not include photopeak photons. The set of images 800 further includes a scatter image 820 acquired with a CZT camera that includes scattered and tailed photopeak photons. A hot spot is clearly visible in the scatter image 820 caused by the tailed photopeak photons. The set of images 800 further includes a corrected scatter image 830 corresponding to the scatter image 820 but corrected for tailed photopeak photons according to the methods described herein. The hot spot clearly visible in the scatter image 820 is reduced in the corrected scatter image 830, such that the corrected scatter image 830 is more consistent with the pure scatter distribution depicted in the scatter image 810.

For clarity, FIG. 9 shows a graph 900 illustrating example distributions for the example scatter images of FIG. 8. In particular, the graph 900 depicts the distribution of photon counts as a function of pixel location in the scatter images 800. The graph 900 includes a plot of the distribution 910 for the scatter image 810, a plot of the distribution 920 for the scatter image 820, and a plot of the distribution 930 for the corrected scatter image 830.

The distribution 920 for the un-corrected scatter image 820 clearly depicts the hot spot caused by the tailed photons. The distribution 930 for the corrected scatter image 830 indicates that the correction techniques described herein accurately correct the scatter distribution such that the distribution 830 resembles the pure scatter distribution 910. That is, by correcting the scatter data to remove tailed photopeak photons, the scatter estimates for CZT detectors may approach the accuracy of scatter estimates of NaI detectors. Scatter correction techniques that were previously unavailable for NM imaging systems configured with CZT gamma cameras due to the tailing effect, such as the dual energy window technique, may thus be performed with such NM imaging systems.

To illustrate the efficacy of the methods provided herein for correcting scatter distributions, FIGS. 10 and 11 depict example images. For example, FIG. 10 shows a set of images 1000 illustrating an example scatter correction according to an embodiment. In particular, the first image 1010 depicts high energy projections as acquired while the second image 1020 depicts low energy projections as acquired. The second image 1020 clearly suggests the presence of tailed photopeak photons, as the second image 1020 resembles the first image 1010 at a lower resolution. Notably, the circular dark object in the first image 1010 is visible in the second image 1020. The third image 1030 depicts corrected scatter projections corresponding to the projections of the second image 1020 with the correction technique provided herein applied thereto. The third image 1030 thus depicts "pure" scatter projections of the second image 1020 with the tailed photopeak photons removed. It should be appreciated that attempting to perform scatter correction of the projection data of the high energy window depicted in the first image 1010 based on the projection data of the low energy window depicted in the second image 1020 would result in the removal of photopeak photons from the high energy window, thereby reducing the accuracy of the scatter correction and lowering the image quality of the final image overall.

Similarly, FIG. 11 shows a set of images 1100 illustrating another example scatter correction according to an embodiment. The set of images 1100 includes a first image 1110 comprising a low-resolution reconstructed high energy window image, a second image 1120 comprising a low-resolution reconstructed low energy window image, and a third image 1130 comprising a pure scatter image corrected for tailed photons. It should be appreciated that attempting to correct the first image 1110 based on the second image 1120 would degrade the overall accuracy and image quality of the first image 1110, as the second image 1120 includes photopeak photons. In contrast, correcting the first image 1110 based on the corrected or pure scatter distribution of the third image 1130 would result in a more accurate scatter correction and thus an improved image quality.

A technical effect of the disclosure includes an improved image quantitative and qualitative accuracy for images acquired with CZT detectors. Another technical effect of the disclosure includes the increased accuracy of scatter correction for NM imaging systems. Yet another technical effect of the disclosure includes the reduction or elimination of photopeak photons from scatter distributions. Another technical effect of the disclosure includes the display of a reconstructed image acquired with CZT detectors with accurate scatter correction applied thereto. Yet another technical effect of the disclosure includes the reduction of computational complexity for accurate scatter correction for images acquired with CZT detectors, as the present methods and systems do not require computationally expensive scatter simulations for scatter correction.

In one embodiment, a method for NM imaging comprises acquiring, with a plurality of detectors, imaging data separated into a high energy window and a low energy window, removing photopeak photons from the imaging data in the low energy window to obtain a corrected scatter distribution, correcting the imaging data based on the corrected scatter distribution, and outputting a scatter-corrected image reconstructed from the corrected imaging data.

In a first example of the method, the method further comprises reconstructing a first image from the imaging data in the high energy window with contrast and resolution matched to scattered photons, and reconstructing a second image from the imaging data in the low energy window with contrast and resolution matched to the scattered photons. In a second example of the method optionally including the first example, reconstructing the first image and the second image with the contrast and the resolution matched to the scattered photons comprises performing iterative reconstruction of the imaging data in the high energy window and the low energy window, respectively, for a reduced number of iterations. In a third example of the method optionally including one or more of the first and second examples, removing the photopeak photon distribution from the imaging data in the low energy window comprises subtracting the first image from the second image to obtain a scatter image of the corrected scatter distribution. In a fourth example of the method optionally including one or more of the first through third examples, correcting the imaging data based on the corrected scatter distribution comprises correcting the imaging data based on the scatter image. In a fifth example of the method optionally including one or more of the first through fourth examples, the method further comprises processing the scatter image by at least scaling the scatter image based on calibration of the plurality of detectors and a calibration of a width and a position of the high energy window and the low energy window. In a sixth example of the method optionally including one or more of the first through fifth examples, the method further comprises weighting the first image with a scaling factor obtained from calibration of the plurality of detectors prior to subtracting the first image from the second image. In a seventh example of the method optionally including one or more of the first through sixth examples, correcting the imaging data based on the corrected scatter distribution comprises using the corrected scatter distribution during iterative reconstruction as a scatter estimate. In an eighth example of the method optionally including one or more of the first through seventh examples, the plurality of detectors comprise CZT detectors.

In another embodiment, a method for NM imaging comprises acquiring, with a plurality of detectors, imaging data separated into a high energy window and a low energy window, reconstructing a first image from the imaging data in the high energy window with a low resolution, reconstructing a second image from the imaging data in the low energy window with a low resolution, correcting the second image according to a photopeak photon distribution known from the first image to obtain a scattered photon distribution image, correcting the imaging data based on the scattered photon distribution image, and outputting a scatter-corrected image reconstructed from the corrected imaging data.

In a first example of the method, correcting the second image according to the photopeak photon distribution known from the first image comprises scaling the first image and subtracting the scaled first image from the second image to obtain the scattered photon distribution image. In a second example of the method optionally including the first example, scaling the first image comprises multiplying the first image by a scaling factor obtained from calibrating the plurality of detectors. In a third example of the method optionally including one or more of the first and second examples, reconstructing the first image from the imaging data in the high energy window comprises performing iterative reconstruction of the imaging data in the high energy window for a limited number of iterations, and reconstructing the second image from the imaging data in the high energy window comprises performing iterative reconstruction of the imaging data in the low energy window for the limited number of iterations. In a fourth example of the method optionally including one or more of the first through third examples, the method further comprises reconstructing the scatter-corrected image by performing iterative reconstruction of the corrected imaging data for a number of iterations greater than the limited number of iterations.

In yet another embodiment, a system comprises a detector array including a plurality of detectors, and a computing device communicatively coupled to the detector array and configured with instructions in non-transitory memory that when executed cause the computing device to: acquire, via the detector array, imaging data separated into a high energy window and a low energy window; remove photopeak photons from the imaging data in the low energy window to obtain a corrected scatter distribution; correct the imaging data based on the corrected scatter distribution; and output a scatter-corrected image reconstructed from the corrected imaging data.

In a first example of the system, the computing device is further configured with instructions in the non-transitory memory that when executed cause the computing device to reconstruct a first image from the imaging data in the high energy window with contrast and resolution matched to scattered photons, and reconstruct a second image from the imaging data in the low energy window with contrast and resolution matched to the scattered photons. In a second example of the system optionally including the first example, reconstructing the first image and the second image with the contrast and the resolution matched to the scattered photons comprises performing iterative reconstruction of the imaging data in the high energy window and the low energy window, respectively, for a reduced number of iterations. In a third example of the system optionally including one or more of the first and second examples, the computing device is further configured with instructions in the non-transitory that when executed cause the computing device to remove the photopeak photons from the imaging data in the low energy window by subtracting the first image from the second image to obtain a scatter image of the corrected scatter distribution, and to correct the imaging data based on the corrected scatter distribution by correcting the imaging data based on the scatter image. In a fourth example of the system optionally including one or more of the first through third examples, the plurality of detectors comprise CZT detectors. In a fifth example of the system optionally including one or more of the first through third examples, the plurality of detectors comprise PET detectors with low energy resolution. In a sixth example of the system optionally including one or more of the first through fifth examples, the system further comprises a display device communicatively coupled to the computing device, wherein the computing device outputs the scatter-corrected image to the display device.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for nuclear medicine (NM) imaging, comprising:
acquiring, with a plurality of detectors, imaging data separated into at least two energy windows including a first energy window and a second energy window, wherein the imaging data in the at least two energy windows includes a photopeak photon distribution and a scattered photon distribution;
separating the scattered photon distribution from the photopeak photon distribution by decomposing the imaging data in the at least two energy windows to obtain a corrected scatter distribution;
reconstructing a scatter-corrected image from the imaging data with the corrected scatter distribution removed; and
outputting the scatter-corrected image.

2. The method of claim 1, further comprising reconstructing a first image from the imaging data in the first energy window with contrast and resolution matched to a contrast and resolution of the scattered photon distribution, and reconstructing a second image from the imaging data in the second energy window with contrast and resolution matched to the contrast and the resolution of the scattered photon distribution.

3. The method of claim 2, wherein reconstructing the first image and the second image with the contrast and the resolution matched to the contrast and the resolution of the scattered photon distribution comprises performing iterative reconstruction of the imaging data in the first energy window and the second energy window, respectively, for a reduced number of iterations.

4. The method of claim 2, wherein separating the scattered photon distribution from the photopeak photon distribution by decomposing the imaging data in the at least two energy windows to obtain the corrected scatter distribution comprises subtracting the first image from the second image to obtain an image of the corrected scatter distribution.

5. The method of claim 4, further comprising correcting the imaging data based on the corrected scatter distribution by correcting the imaging data in the first energy window in image space based on the image of the corrected scatter distribution.

6. The method of claim 5, further comprising processing the image of the corrected scatter distribution by at least scaling the image of the corrected scatter distribution based on calibration of the plurality of detectors and a calibration of a width and a position of the first energy window and the second energy window.

7. The method of claim 4, further comprising weighting the first image with a scaling factor obtained from calibration of the plurality of detectors prior to subtracting the first image from the second image.

8. The method of claim 2, wherein separating the scattered photon distribution from the photopeak photon distribution by decomposing the imaging data in the at least two energy windows to obtain the corrected scatter distribution comprises iteratively decomposing the first image from the second image to obtain an image of the corrected scatter distribution.

9. The method of claim 1, further comprising correcting the imaging data based on the corrected scatter distribution by using the corrected scatter distribution during iterative reconstruction as a scatter estimate.

10. A method for NM imaging, comprising:
acquiring, with a plurality of detectors, imaging data separated into a high energy window and a low energy window;
reconstructing a first image from the imaging data in the high energy window with a low resolution to match a scattered photon distribution;
reconstructing a second image from the imaging data in the low energy window with a low resolution to match the scattered photon distribution;
correcting the second image by eliminating photopeak photons in the second image according to a photopeak photon distribution known from the first image to obtain a scattered photon distribution image;
correcting the imaging data based on the scattered photon distribution image to obtain scatter-corrected imaging data; and
outputting a scatter-corrected image reconstructed from the scatter-corrected imaging data.

11. The method of claim 10, wherein correcting the second image according to the photopeak photon distribution known from the first image comprises scaling the first image and subtracting the scaled first image from the second image to obtain the scattered photon distribution image.

12. The method of claim 11, wherein scaling the first image comprises multiplying the first image by a scaling factor obtained from calibrating the plurality of detectors.

13. The method of claim 10, wherein reconstructing the first image from the imaging data in the high energy window comprises performing iterative reconstruction of the imaging data in the high energy window for a limited number of iterations, and wherein reconstructing the second image from the imaging data in the high energy window comprises performing iterative reconstruction of the imaging data in the low energy window for the limited number of iterations.

14. The method of claim 13, further comprising reconstructing the scatter-corrected image by performing iterative reconstruction of the corrected imaging data for a number of iterations greater than the limited number of iterations.

15. A system, comprising:
a detector array including a plurality of detectors; and
a computing device communicatively coupled to the detector array and configured with instructions in non-transitory memory that when executed cause the computing device to:
acquire, via the detector array, imaging data separated into a high energy window and a low energy window;
determine a photopeak photon distribution from the imaging data in the high energy window;
remove photopeak photons from the imaging data in the low energy window according to the photopeak photon distribution to obtain a corrected scatter distribution;
correct the imaging data based on the corrected scatter distribution; and
output a scatter-corrected image reconstructed from the corrected imaging data.

16. The system of claim 15, wherein the computing device is further configured with instructions in the non-transitory memory that when executed cause the computing device to: reconstruct a first image from the imaging data in the high energy window with contrast and resolution matched to scattered photons, and reconstruct a second image from the imaging data in the low energy window with contrast and resolution matched to the scattered photons.

17. The system of claim 16, wherein reconstructing the first image and the second image with the contrast and the resolution matched to the scattered photons comprises performing iterative reconstruction of the imaging data in the high energy window and the low energy window, respectively, for a reduced number of iterations.

18. The system of claim 16, wherein the computing device is further configured with instructions in the non-transitory that when executed cause the computing device to remove the photopeak photons from the imaging data in the low energy window by subtracting the first image from the second image to obtain a scatter image of the corrected scatter distribution, and to correct the imaging data based on the corrected scatter distribution by correcting the imaging data based on the scatter image.

19. The system of claim 15, wherein the plurality of detectors comprise CZT detectors.

20. The system of claim 15, wherein the plurality of detectors comprise PET detectors with low energy resolution.

21. The system of claim 15, further comprising a display device communicatively coupled to the computing device, wherein the computing device outputs the scatter-corrected image to the display device.

* * * * *